US00PP33188P2

(12) United States Plant Patent
Kim

(10) Patent No.: US PP33,188 P2
(45) Date of Patent: Jun. 22, 2021

(54) ***PHLOX* PLANT NAMED 'BALSUKAPIN'**

(50) Latin Name: *Phlox paniculata*
Varietal Denomination: Balsukapin

(71) Applicant: Ball Horticultural Company, West Chicago, IL (US)

(72) Inventor: Grace H. Kim, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/005,980

(22) Filed: Aug. 28, 2020

(51) Int. Cl.
*A01H 5/02* (2018.01)
*A01H 6/70* (2018.01)

(52) U.S. Cl.
USPC ..... Plt./320
CPC ..... *A01H 6/70* (2018.05)

(58) Field of Classification Search
USPC ..... Plt./320
CPC ..... A01H 5/02
See application file for complete search history.

(56) References Cited

U.S. PATENT DOCUMENTS

PP30,779 P2 * 8/2019 Kievit ..... A01H 6/70
Plt./320

OTHER PUBLICATIONS file:///C:/Users/kbell/Downloads/2020%20Eval%20Day%20Booklet.pdf; Aug. 3, 2020; 2 pages.*
https://www.darwinperennials.com/Products/plantinfo/?phid=049209033004054; Dec. 11, 2020; 2 pages.*

* cited by examiner

*Primary Examiner* — Kent L Bell
(74) *Attorney, Agent, or Firm* — Audrey Charles

(57) ABSTRACT

A new and distinct cultivar of *Phlox* plant named 'Balsukapin', characterized by its medium reddish-purple colored flowers, medium green-colored foliage, and vigorous, upright growth habit, is disclosed.

1 Drawing Sheet

Latin name of genus and species of plant claimed: *Phlox paniculata.*

Variety denomination: 'Balsukapin'.

BACKGROUND OF THE INVENTION

The present invention relates to a new and distinct cultivar of *Phlox* plant botanically known as *Phlox paniculata* and hereinafter referred to by the cultivar name 'Balsukapin'.

The new cultivar originated in a controlled breeding program in Guadalupe, Calif. during June 2014. The objective of the breeding program was the development of *Phlox* cultivars with large sized flowers, increased powdery mildew resistance and a vigorous, upright growth habit.

The new *Phlox* cultivar is the result of cross-pollination. The female (seed) parent of the new cultivar is 'Jade', U.S. Plant Pat. No.21,878, characterized by its blush-pink colored flowers with green-colored tips, medium green-colored foliage, and moderately vigorous, upright growth habit. The male (pollen) parent of the new cultivar is the proprietary *Phlox paniculata* breeding selection coded PHL-742, not patented, characterized by its medium purple-colored flowers, medium green-colored foliage, and moderately vigorous, upright growth habit. The new cultivar was selected as a single flowering plant within the progeny of the above stated cross-pollination during August 2015 in a controlled environment in Guadalupe, Calif.

Asexual reproduction of the new cultivar by terminal stem cuttings since August 2015 in Guadalupe, Calif. and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balsukapin' as a new and distinct cultivar of *Phlox* plant:

1. Medium reddish-purple colored flowers;
2. Medium green-colored foliage; and
3. Vigorous, upright growth habit.

Plants of the new cultivar differ from plants of the female parent primarily in having medium reddish-purple colored flowers and increased branching. Plants of the new cultivar differ from plants of the male parent primarily in having medium reddish-purple colored flowers, increased branching, and increased growth vigor.

Of the many commercially available *Phlox* cultivars, the most similar in comparison to the new cultivar is KA-POW Pink 'Balkapopink', U.S. Plant Pat. No. 30,779. However, in side by side comparisons, plants of the new cultivar differ from plants of 'Balkapopink' in at least the following characteristics:

1. Plants of the new cultivar have larger primary and secondary inflorescences than plants of 'Balkapopink';
2. Plants of the new cultivar have larger diameter flowers than plants of 'Balkapopink'; and
3. Plants of the new cultivar have a medium reddish-purple flower color that is different from the rose-pink colored flowers of plants of 'Balkapopink'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balsukapin'. The plants were approximately five months old. The plants were grown in one-gallon containers for approximately 12 weeks in an outdoor nursery in West Chicago, Ill. Plants were given two pinches prior to transplant.

DETAILED BOTANICAL DESCRIPTION

Figure 1:
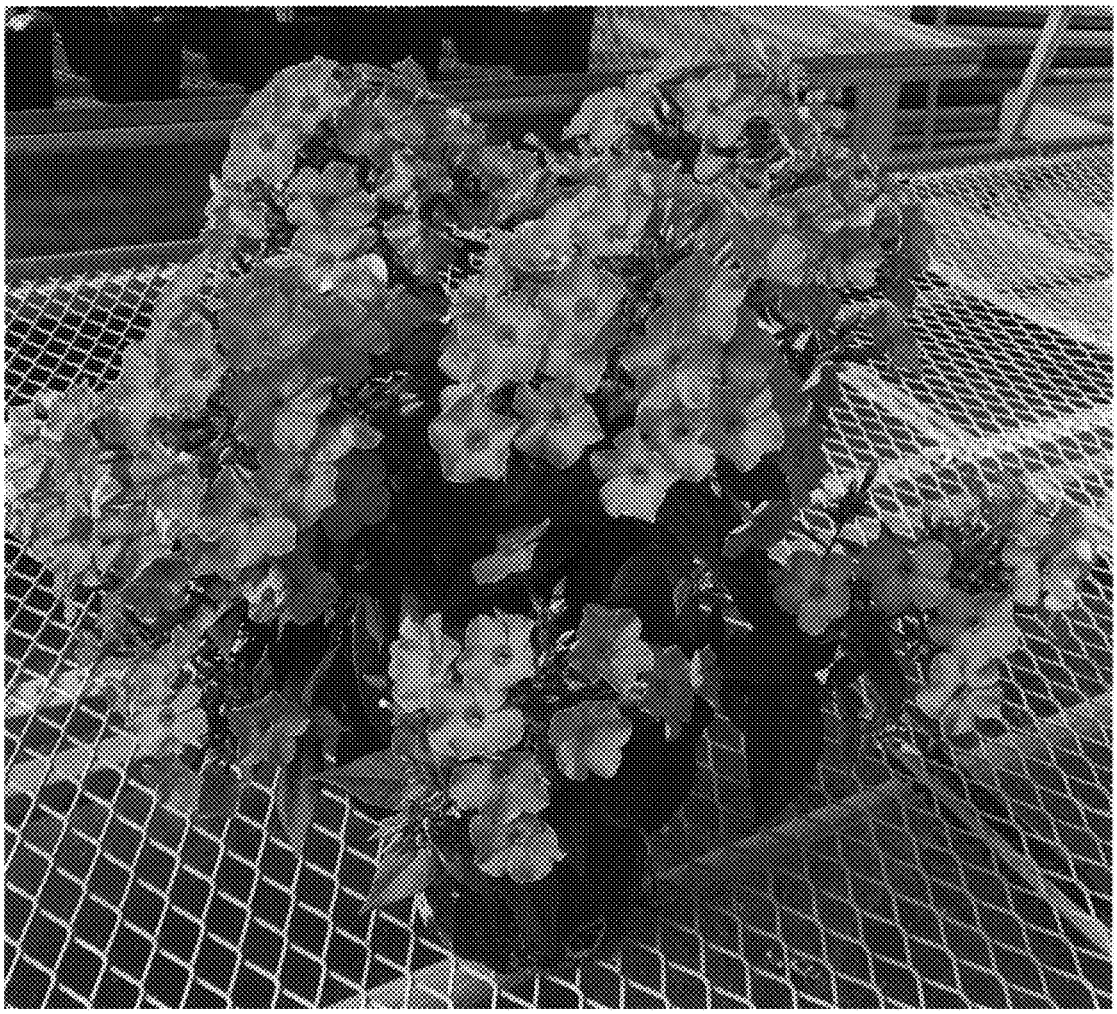
FIG. 1 illustrates a side view of the overall growth and flowering habit of 'Balsukapin'.
Figure 2:
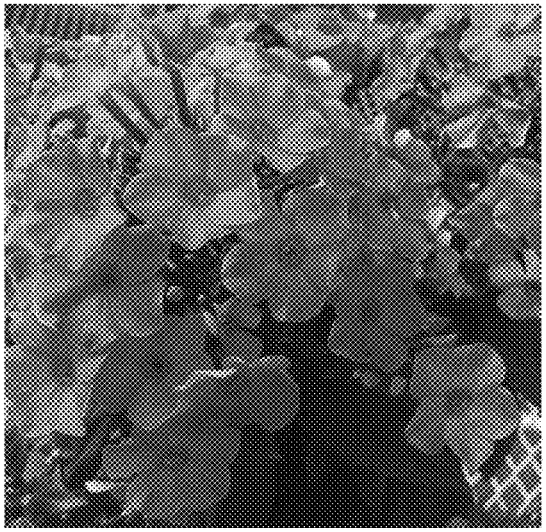
FIG. 2 illustrates a close-up view of an individual inflorescence of 'Balsukapin'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The RHS Colour Chart of The Royal Horticultural Society, London, England, 2015 edition, except where general color terms of ordinary significance are used. The color values were determined in July 2020 under natural light conditions in Naperville, Ill.

The following descriptions and measurements describe approximately five-month old plants produced from cuttings from stock plants and grown under conditions comparable to those used in commercial practice. The plants were grown in one-gallon containers for approximately 12 weeks in an outdoor nursery in West Chicago, Ill. Plants were given two pinches prior to transplant. Prior to transplant plants were grown in liners in a poly-covered greenhouse in West Chicago, Ill. Greenhouse temperatures ranged from an average high of 69.3° F. (20.7° C.) to an average low of 63.6° F. (17.6° C.), and supplemental lighting was provided daily for five hours during short days. Measurements and numerical values represent averages of typical plants.

Botanical classification: *Phlox paniculata* 'Balsukapin'.

Parentage:

*Female parent.*—'Jade', U.S. Plant Pat. No.21,878.

*Male parent.*—Proprietary *Phlox paniculata* breeding selection coded PHL-742, not patented.

Propagation:

*Type cutting.*—Terminal stem.

*Time to initiate roots.*—Approximately 10 to 12 days.

*Time to produce a rooted cutting.*—Approximately 42 to 49 days.

*Root description.*—Fine to medium thickness, medium density.

*Rooting habit.*—Freely branching, medium density.

Plant description:

*Commercial crop time.*—Approximately 10 to 12 weeks from a rooted cutting to finish in a 15 cm pot.

*Growth habit and general appearance.*—Herbaceous perennial, vigorous, upright growth habit.

*Hardiness.*—USDA Zone 4b (−20° F. to −25° F./−28.9° C. to −31.7° C.).

*Size.*—Height: Approximately 33.5 cm. Width: Approximately 48.0 cm.

*Branching habit.*—Freely branching, pinching will improve branching.

*Branch.*—Quantity: Approximately 7 main branches. Shape: Round. Strength: Strong. Length to base of inflorescence: Approximately 13.0 cm. Diameter: Approximately 3.0 mm to 4.0 mm. Length of central internode: Approximately 1.6 cm. Texture: Glabrous. Color of young stems: 146B with a small overlay of N187A at node. Color of mature stems: 146B with a small overlay of N187A at node, becoming woody 199B with age.

Foliage description:

*General description.*—Quantity of leaves per main branch: Approximately 16. Fragrance: None detected. Form: Simple. Arrangement: Opposite, decussate.

*Leaves.*—Shape: Elliptic, slightly carinate. Margin: Entire, minutely ciliate. Apex: Acute. Base: Attenuate. Venation pattern: Pinnate. Length: Approximately 9.0 cm. Width: Approximately 3.8 cm. Texture of upper surface: Sparsely pubescent. Texture of lower surface: Glabrous. Color of upper surface of young foliage: 137B with venation of 146D. Color of lower surface of young foliage: Closest to 147B with venation of 146D. Color of upper surface of mature foliage: 137A with venation of 146D. Color of lower surface of mature foliage: Closest to 147B with venation of 146D.

*Petioles.*—Length: Approximately 3.0 mm. Width: Approximately 3.0 mm. Texture: Glabrous. Color: 146D.

Flowering description:

*Flowering habit.*—'Balsukapin' is a long day obligate and is freely flowering under outdoor growing conditions with substantially continuous blooming from late spring throughout summer.

*Lastingness of individual flower on the plant.*—Approximately 10 days.

Inflorescence description:

*General description.*—Type: Compound terminal panicle, flowers face upright and outwardly, self-cleaning. Quantity per plant: Approximately 7. Fragrance: Moderately sweet and pleasant. Height of primary: Approximately 10.0 cm. Width of primary: Approximately 14.0 cm. Quantity of fully open flowers per primary inflorescence: Approximately 35. Height of secondary: Approximately 6.5 cm. Width of secondary: 8.0 cm. Quantity of fully open flowers per secondary inflorescence: Approximately 6.

*Peduncle.*—Strength: Strong. Aspect: Primary erect, axillary acute angle to stem. Length of primary: Approximately 2.0 cm. Diameter of primary: Approximately 3.0 mm. Length of axillary: Approximately 1.5 cm. Diameter of axillary: Approximately 2.0 mm. Texture: Moderately pubescent. Color: 146B tinted with N187A.

Flower description:

*Type.*—Single.

*Bud.*—Rate of opening: Generally takes 3 to 4 days for bud to progress from first color to fully open flower.

*Bud just before opening.*—Shape: Oblanceolate. Length: Approximately 1.5 cm. Diameter: Approximately 4.0 mm. Color: Calyx of 145A with N186A at tips and petal portion of 75A to 75B.

*Corolla.*—Shape: Salverform. Diameter: Approximately 3.4 cm. Depth: Approximately 3.2 cm.

*Petals.*—Quantity: 5 in a single whorl, base fused into a narrow tube. Lobe shape: Obovate. Margin: Entire. Apex: Obtuse. Lobe length: Approximately 1.5 cm. Lobe width: Approximately 1.6 cm. Texture of upper and lower surfaces: Smooth, glabrous. Color of upper surface when first open: NN74A to NN74C, 67A at orifice. Color of lower surface when first open: 76B to 76C with N78D. Color of upper surface when fully open: NN74B to NN74D, 67A at orifice. Color of lower surface when fully open: 76C with N78D.

*Corolla tube.*—Length: Approximately 2.3 cm. Diameter at distal end: Approximately 3.0 mm. Diameter at proximal end: Approximately 2.0 mm. Texture of outer surface: Moderately pubescent. Texture of inner surface: Smooth, glabrous with lower 6.0 mm densely pubescent. Color of inner surface: N81C with 145D at base. Color of outer surface: N78B to N78C, 145D at base.

*Calyx.*—Shape: Cupped. Length: Approximately 9.0 mm. Diameter: Approximately 3.0 mm.

*Sepals.*—Quantity per flower: 5, lower half fused. Shape: Lanceolate. Margin: Entire. Apex: Narrowly apiculate. Length: Approximately 9.0 mm. Width: Approximately 2.0 mm. Texture of outer surface: Sparsely pubescent. Texture of inner surface: Smooth, glabrous. Color of inner surface: 145A with tip of N186A. Color of outer surface: 145A with tip and faint central streak of N186A.

*Pedicel.*—Strength: Strong, flexible. Aspect: Primary erect, axillary acute angle to peduncle. Length: Approximately 4.0 mm. Diameter: Approximately 1.0 mm. Texture: Densely pubescent. Color: 146B.

*Reproductive organs.*—Androecium: Stamen quantity: 5 per flower, adnate to corolla tube. Stamen length: Approximately 2.2 cm. Filament length of free portion: Approximately 1.0 mm. Anther shape: Sagittate. Anther length: Approximately 2.0 mm. Anther color: 158B. Pollen amount: Abundant. Pollen color: 155D. Gynoecium: Pistil quantity: 1 per flower. Pistil length: Approximately 2.3 cm. Stigma shape: Cleft, three-parted. Stigma length: Approximately 1.0 mm. Stigma color: 150D. Style length: Approximately 2.1 cm. Style color: 145D. Ovary length: Approximately 2.0 mm. Ovary color: 144A.

Seed and fruit production: Neither seed nor fruit production has been observed.

Disease and pest resistance: Increased resistance to powdery mildew has been observed.

What is claimed is:

1. A new and distinct cultivar of *Phlox* plant named 'Balsukapin', substantially as herein illustrated and described.

* * * * *